(12) United States Patent
Michael

(10) Patent No.: US 6,456,199 B1
(45) Date of Patent: Sep. 24, 2002

(54) CONTINUOUS NOISE MONITORING AND REDUCTION SYSTEM AND METHOD

(75) Inventor: Kevin Michael, State College, PA (US)

(73) Assignee: doseBusters USA, Pittsburgh, PA (US)

( * ) Notice: Subject to any disclaimer, the term of this patent is extended or adjusted under 35 U.S.C. 154(b) by 0 days.

(21) Appl. No.: 09/788,126

(22) Filed: Feb. 16, 2001

Related U.S. Application Data

(60) Provisional application No. 60/183,639, filed on Feb. 18, 2000.

(51) Int. Cl.7 ............................................... G08B 23/00
(52) U.S. Cl. .................................... 340/573.1; 340/540
(58) Field of Search ............................ 340/573.1, 540, 340/261; 381/72, 56; 73/646

(56) References Cited

U.S. PATENT DOCUMENTS

| | | | | |
|---|---|---|---|---|
| 3,697,973 A | * | 10/1972 | Stevens et al. | 340/261 |
| 3,802,535 A | * | 4/1974 | Peake et al. | 181/5 |
| 3,848,471 A | * | 11/1974 | Hamburg et al. | 73/557 |
| 3,968,334 A | * | 7/1976 | Padilla | 179/175 |
| 4,020,298 A | | 4/1977 | Epley et al. | |
| 4,060,701 A | * | 11/1977 | Epley | 179/175 |
| 4,307,385 A | * | 12/1981 | Evans et al. | 340/540 |
| 5,317,273 A | * | 5/1994 | Hanson et al. | 324/616 |
| 5,757,930 A | | 5/1998 | Seidemann et al. | |

* cited by examiner

Primary Examiner—Thomas Mullen
Assistant Examiner—Son Tang
(74) Attorney, Agent, or Firm—Crowell & Moring LLP

(57) ABSTRACT

An apparatus adapted to be worn in an environment in which unsafe noise levels may be present for the purpose of continuously monitoring the noise level impinging upon the ear(s) of a user. The noise levels are monitored via a microphone housed within a hearing protective device, and located such that the noise level measured by the microphone is representative of the noise level impinging upon the ear(s) of the user when the hearing protective device is being worn in either a primary or secondary position. The noise level is recorded along with its duration to calculate a cumulative noise dose for an individual user, and to warn the user of when the noise dose exceeds a preset level. The apparatus further provides for a means of transmitting the noise level and dose information to a data storage/retrieval device such as a PC for maintaining a history of noise exposure for the individual user of the device. A method of using an apparatus as described, or a similar device, to continuously monitor an individual's noise exposure is also disclosed.

30 Claims, 10 Drawing Sheets

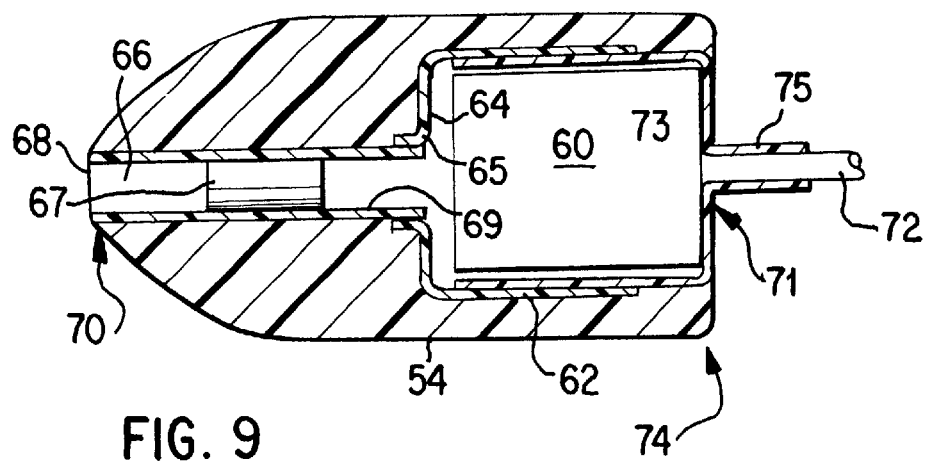
FIG. 9
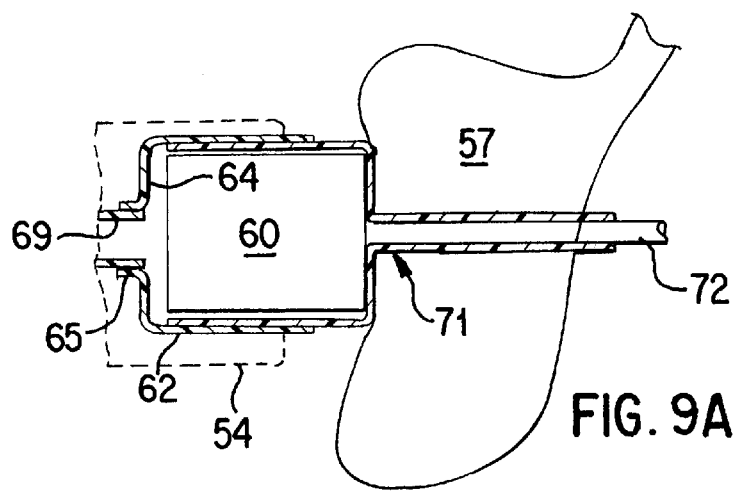
FIG. 9A
FIG. 4
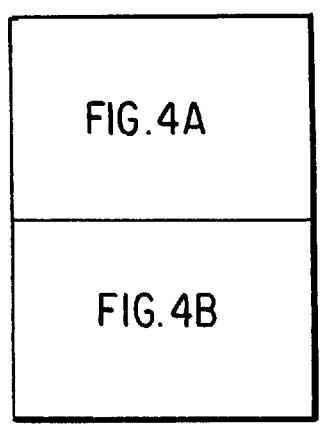
FIG. 10
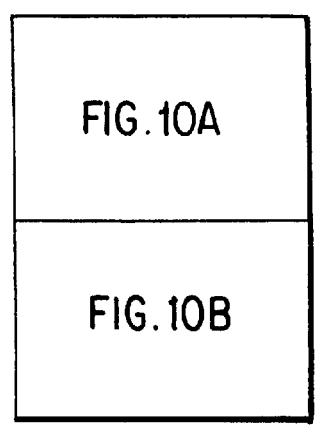

CONTINUOUS NOISE MONITORING AND REDUCTION SYSTEM AND METHOD

CROSS-REFERENCE TO RELATED APPLICATION

This application is co-pending with U.S. Provisional Application No. 60/183,639 filed Feb. 18, 2000. The benefit of the filing date of that application is hereby claimed.

TECHNICAL FIELD OF THE INVENTION

The present invention relates to a noise monitoring system, and in particular to a noise monitoring system and method for continuously and accurately monitoring an individual's noise exposure during periods when an individual's hearing protective device is occluding the ear, and when such device is being worn in an off-the-ear position.

BACKGROUND OF THE INVENTION

The U.S. Department of Labor Occupational Noise Exposure Standard (29 C.F.R. § 1910.95) specifies that noise dosimetry may be used to measure noise exposure on individuals in the workplace. The standard specifies that individuals exposed to greater than 85 dBA Time-Weighted Average ("TWA") must be included in a comprehensive hearing conservation program ("HCP"). The allowable exposure to noise is measured in terms of cumulative noise dose, i.e., individuals are considered to be within compliance if they are exposed to less than 90 dBA TWA (a 100% dose) over an 8 hour work day. Total noise dose during the work day is given by $D=100$ $(C_1/T_1+C_2/T_2 + \ldots C_n/T_n)$, where D is the percentage noise dose, C is the total length of the specific exposure, in hours, and T is the reference duration corresponding to the measured sound level (see 29 C.F.R. § 1910.95, Table G-16A, 1999). A TWA of the A-weighted sound level may be calculated from the dose measurement by means of the formula: $TWA=16.61 \log_{10}(D/100)+90$. This provides a mechanism for accumulating exposures of varying levels and durations where an "exchange rate" of 5 dB per doubling of time is used to evaluate exposure levels. For example, an exposure of 90 dBA for 4 hours is considered equivalent to either 1) an exposure of 85 dBA for 8 hours, or 2) an exposure of 95 dBA for 2 hours. Noise dosimeters are employed to measure cumulative noise dose by applying the "exchange rate" to the level and duration of exposure.

Noise dosimetry is commonly used in industry, and the measurements are usually intended to indicate the cumulative exposure to noise over the course of a full work shift. In addition to determining which employees should be included in the HCP, these measurements are commonly used to determine hearing protector requirements, and to determine noise control requirements. The information gathered by noise dosimeters is typically used by industrial personnel only, i.e., this information is not intended for interpretation by the worker. In many instances, the readouts of dosimeters are sealed shut so that the wearer has no visible indication of current exposure or dose.

Currently existing hearing protective devices ("HPD") such as ear muffs, ear plugs, and semi-aural devices, provide widely variable attenuation in the workplace and the laboratory ratings of a HPD's performance may grossly overestimate the protection afforded some individuals. There are several methods of measuring the effectiveness of hearing protectors on the end-users, but these methods are point measurements, i.e., measurements made to determine the attenuation provided by the HPDs after one fitting of the device. Point measurement apparatus and methods are described in Epley (U.S. Pat. Nos. 4,060,701; 4,020,298); Padilla (U.S. Pat. No. 3,968,334); and Seidemann (U.S. Pat. No. 5,757,930). A major disadvantage of evaluating hearing protector effectiveness by point measurement is that no insight is provided into the actual protection afforded the HPD wearer at any time, or period of time, other than during the measurement session.

Continuous monitoring of personal noise exposure with conventional hardware is both cumbersome and prohibitively expensive. Conventional noise dosimeters are not intended for use on every employee during every work shift, and are far too expensive to be used on a daily basis on every employee.

Conventional noise dose measurements are intended to be performed with the dosimeter microphone mounted on the shoulder of the employee. This microphone placement technique accurately measures noise dose, but does not take into account the noise reduction provided by the HPD. While it is possible to mount the conventional dosimeter microphone inside a muff-type HPD to measure noise dose while wearing muffs, the hardware configuration is awkward, prohibitively expensive, and not suitable for everyday use.

Evans (U.S. Pat. No. 4,307,385) describes a noise monitoring device, but it is not designed for accurate measurements when not being worn by the user in an over the ear position. This is a major disadvantage of the Evans system since the overall accuracy of measurements will be compromised during periods when the HPD is not donned. The Evans system measures noise exposure when the HPD is worn, but the system does not measure the overall noise exposure to the hearing protector wearer over the course of an average workday, which includes periods when the HPD is not donned.

Damage-risk criteria for predicting the incidence of noise-induced hearing loss ("NIHL") among populations of workers as a function of workplace noise levels and exposures are the basis of all current occupational noise regulations in the United States. The development of these fundamental damage-risk criteria is based primarily on an assessment of workplace noise levels as measured in a diffuse field at the worker's center-of-head ("COH") location, but with the worker absent. Thus, it is of the utmost importance that any determination of a worker's protected, or unprotected, noise exposure be correlated to an equivalent COH dose. For example, the popular top-of-the-shoulder microphone location utilized for conducting a personal noise dosimeter measurement of a worker's unprotected noise exposure is simply a convenient and practical surrogate for the true COH location. Measurement of a worker's noise dose using this substitute location provides a reasonably accurate approximation of the worker's true COH noise exposure for most industrial acoustical conditions. However, other locations in the vicinity of the worker's head, or in the ear, are just as suitable as surrogates, especially with the availability of miniature microphones.

Workers in the United States continue to experience an unacceptably high incidence of NIHL despite the existence of federal legislation designed to prevent such injuries. Much of the current state of hearing conservation can be attributed directly to the reliance, over the last 30 years, on limited or single-shift noise exposure data and personal hearing protection as the first, and only, line of defense against hazardous noise. Moreover, past efforts to protect workers from occupational noise have focused primarily on achieving compliance with the noise regulations, rather than prevention. While a single shift measurement of noise exposure is sufficient for compliance purposes, it fails to account for the highly variable daily noise exposures found in general industry. Numerous studies have also documented that the deficiencies associated with personal hearing protectors and their use make it virtually impossible to accurately predict, based on laboratory-derived performance data, their effectiveness in reducing workplace noise exposures. As a result of this ambiguity in both short and long-term noise exposures, many workers have remained overexposed. No strategy to prevent NIHL will ever be effective until this ambiguity in worker noise exposure is eliminated. Thus, a new solution is needed to resolve this ambiguity and facilitate the upstream prevention of NIHL.

The current invention is a system and method for reducing noise exposure and for the continuous monitoring of personal noise exposure. It involves the integration of personal noise dosimetry with a standard hearing protector in such a manner that, the worker's actual noise exposure is accurately measured under all acceptable wearing conditions. Analytical and empirical techniques demonstrate that the surrogate primary and secondary microphone measurement locations, as defined and employed in the subject system and method, yield noise exposures that are accurate estimates of their equivalent COH noise exposures. The method and apparatus take into account all the factors contributing to exposure ambiguity, such as fit and wearing time, that otherwise limit and ultimately control the effectiveness of a traditional hearing protector. An integral part of the system and method of the present invention is continuous monitoring, which can be used to ensure that a worker is protected to a safe noise exposure level on a daily basis, as well as to document the worker's long-term noise exposure.

Consequently, there is a need for a device that provides a means of continuously monitoring an individual's actual noise exposure rather than simply measuring either hearing protector attenuation or unprotected individual exposure.

SUMMARY OF THE INVENTION

There has now been invented and disclosed herein, a certain new and novel system and method for reducing noise exposure, and for the continuous monitoring of personal noise exposure. The method is cost-effective and unobtrusive, therefore the noise exposure may be continuously monitored for every noise exposed employee during every work shift. The monitoring system includes at least one microphone, housed in the interior of a hearing protective device. The system is unique as it is designed to accurately measure the noise level impinging on the ear of the noise exposed employee both when the hearing protector(s) are occluding the ear, and when they are removed and worn in a secondary, off-the-ear position.

A preferred method of measuring noise exposure on the hearing protector wearer is to continuously monitor and analyze the noise impinging on the ear taking into consideration the effectiveness of the HPD. This type of monitoring requires the use of a noise dosimeter, and the dosimeter microphone must be located interior to the HPD so that the protected, as well as the unprotected noise exposure can be accurately measured.

The current invention is a continuous monitoring device ("CMD"). The CMD performs two functions: 1) it houses the microphone and noise dosimetry hardware; and 2) it reduces noise exposure by physically blocking noise that is incident to the ear. These personal noise exposure measurements do not rely on any laboratory estimates of HPD performance and they are intended to be performed daily, avoiding the inherent inaccuracy associated with spot sampling of noise exposure. Over a period of time the data gathered represent a complete noise exposure history during the employees' work tenure. This type of exposure history may be valuable to the employer if the employee should seek compensation for work-related hearing loss, since the continuous measurements are performed daily, and will definitively determine if noise exposure is incurred on or off the job.

These data are available for analysis on a daily basis, so the employer can take corrective action in the event of excessive exposure to noise. Noise induced hearing loss typically occurs when hearing protectors are worn ineffectively over a long period of time, i.e., after months or years of excessive exposure. If insufficient protection by the CMD is noted and corrected by the employer after one day or a few days of excessive measurements, noise induced hearing loss will not occur.

It is unrealistic to assume that the worker will wear hearing protectors during the entire work shift. Hearing protectors, in fact, should be removed during periods of relative quiet to enhance the overall safety of the worker. An important and unique aspect of the current invention is that the CMD samples the noise impinging on the microphone both when the CMD is worn in or over the ear, and when the CMD is worn off the ear in a secondary position, thereby calculating the total noise dose incident to the wearer's ear. Thus, the CMD is intended to be worn in either primary or secondary positions during the entire work shift: the primary position is defined as over the ears (for muff-type CMD) or inserted into the ear canals (for insert-type or semi-aural CMD) and the secondary position is defined as an acceptable manner of wearing the device without occluding the ear.

For a muff-type continuous monitoring device, one acceptable secondary position is wearing the muff headband around the neck with the muff cups extending forward under the user's chin. For a muff-type continuous monitoring device mounted on a safety-cap, secondary positions include rotating the muff cups up, forward or backward on the safety cap. Thus, there are several defined secondary positions for this configuration. For a semi-aural device an acceptable secondary position is similar to the muff-type CMD, with the headband worn around the neck with the plugs oriented forward, under the user's chin. For insert-type CMD wearers, an acceptable secondary position is to lay the devices on the user's upper chest area with a connecting cord around the back of the neck. The wearing of hearing protectors in a secondary position is commonly done by noise-exposed workers and it is not an undue burden on the employee or the employer. Moreover, it is easy for the employer to visually monitor the use of the CMD, ensuring that it is worn in either the primary or an acceptable secondary position.

The current invention provides a method and system allowing accurate measurement of noise exposure over the course of the entire workday, wherein the typical workday includes periods when the CMDs are worn and periods when they are not worn. When the CMD is worn in the primary position (over the ear or inserted into the ear canal), the microphone is acoustically coupled to the entrance to the ear, measuring the noise level impinging on the ear. When the muff-type CMD is worn in a secondary position, careful consideration of microphone placement, cup construction, and filler foam type and location ensures that measurements will be indicative of the noise level impinging on the ear.

When the insert-type or semi-aural CMD is worn in a secondary position, careful consideration of microphone placement, acoustic filter and coupling tube characteristics ensures that measurements will be indicative of the noise level impinging on the ear. Comparison measurements have been undertaken, and verify that the secondary position CMD microphone measurements are representative of the ambient environmental noise level impinging on the ear.

The average U.S. industrial noise exposure level is about 95 dBA, therefore only about 10–15 dBA of overall protection is usually required to reduce exposure to a safe level. If the CMD is worn effectively, i.e., during periods of high ambient noise levels, the resultant exposure to the ear will be reduced to a safe level in a great majority of typical industrial noise environments. If an excessive daily noise dose is measured by the CMD, it is likely that the device is being worn in the secondary position (off the ear) during periods of high ambient noise. In this case, the wearer must be educated and trained to wear the CMD more consistently.

An additional unique feature of the current invention is a pre-action level warning. This warning, either visual, auditory, or tactile, indicates when the CMD wearer has been exposed to a cumulative dose that is approaching the action level, which is considered to be the cumulative noise dose at which noise-induced hearing damage may occur. Exposures below the action level are, in general, considered to be safe. An administrative action should take place when the pre-action level warning is given, and may include a requirement that the employee wear the CMD in the primary position (over the ears) for the remainder of the work day or relocate out of the noisy environment. The current invention is fully programmable, allowing easy manipulation of exchange rate, criterion level, threshold level, and pre-action level warnings.

In addition, the current invention may also include an instantaneous level warning. This warning, which also may be either visual, auditory, or tactile, indicates when the CMD wearer is currently being exposed to a potentially hazardous noise level. This indicates that either 1) the CMDs should be donned to reduce the exposure level to the ear; 2) the CMDs are not donned in an effective manner, and should be adjusted to further reduce noise exposure to a safe level; or 3) if the CMDs are donned correctly, that the noise exposure level is high enough that the particular type of CMD being used is not sufficient for the level of noise to which the wearer is being exposed. In this latter case, an alternative CMD, or double-protection, i.e. muffs and plugs, should be considered.

A visual alarm may be in the form of a warning light positioned on the HPD or other dosimeter hardware such that it is noticeable to a wearer of the CMD when a pre-action level warning is triggered. Similarly, an audible alarm may be a buzzer or other tone which alerts the CMD wearer to the approaching noise over-exposure. Either type of warning indicator is effective, however, visual alarms may be limited because of the difficulty for a CMD wearer to see a visual alarm attached to an earmuff or other hardware. Audible alarms also have the disadvantage in that they must be louder than the ambient noise in order to be heard.

As an alternative, a tactile warning indicator which includes a vibrator circuit responsive to a high noise condition, functions as a pre-action level warning indicator without the above-mentioned limitations. In a preferred embodiment, the vibrator circuit comprises a pager-motor that vibrates for two seconds when a preset noise level or dose level is exceeded as discussed more fully herein. These vibrations may be repeated at various intervals to ensure that the warning is effectively delivered to the CMD wearer. The pager-motor may be mounted to the circuit board in a muff-type CMD or to other dosimeter hardware in the case of insert-type or semi-aural CMDs.

Another unique aspect of the invention is a wireless readout of cumulative noise dose, duration of measurement, percent of allowable noise dose, calibration check and unit serial number. This aspect of the invention provides a means for a simple and hands-free method for every employee to record the measurements on an everyday basis. In one embodiment of the wireless readout system, an infrared transmitter is mounted on the exterior of the muff cup, and the receiver of the infrared signal is attached to a PC data port. The users will then pass their CMD near the infrared receiver at the end of the work shift, and a software program resident on the PC will read the cumulate noise dose, duration of measurement, and related information via the infrared receiver hardware.

Other important objects, features, and advantages of the invention will be apparent to the reader from the foregoing and the appended claims and as the ensuing detailed description and discussion of the invention is read in conjunction with the accompanying drawings.

BRIEF DESCRIPTION OF THE VARIOUS VIEWS OF THE DRAWINGS

In the drawings, like reference numerals refer to like parts throughout the various views, unless otherwise indicated, and wherein:

FIG. 4 illustrates the arrangement of FIGS. 4A & 4B.

FIG. 9 is a cross-sectional view of a typical insert-type CMD illustrating the arrangement of the microphone and microphone enclosure;

FIG. 9A is a cross-sectional view like FIG. 9 illustrating how the microphone is connected to the headband of a typical semi-aural CMD;

FIG. 10 illustrates the arrangement of FIGS. 10A & 10B.

DETAILED DESCRIPTION OF THE INVENTION

Figure 1:
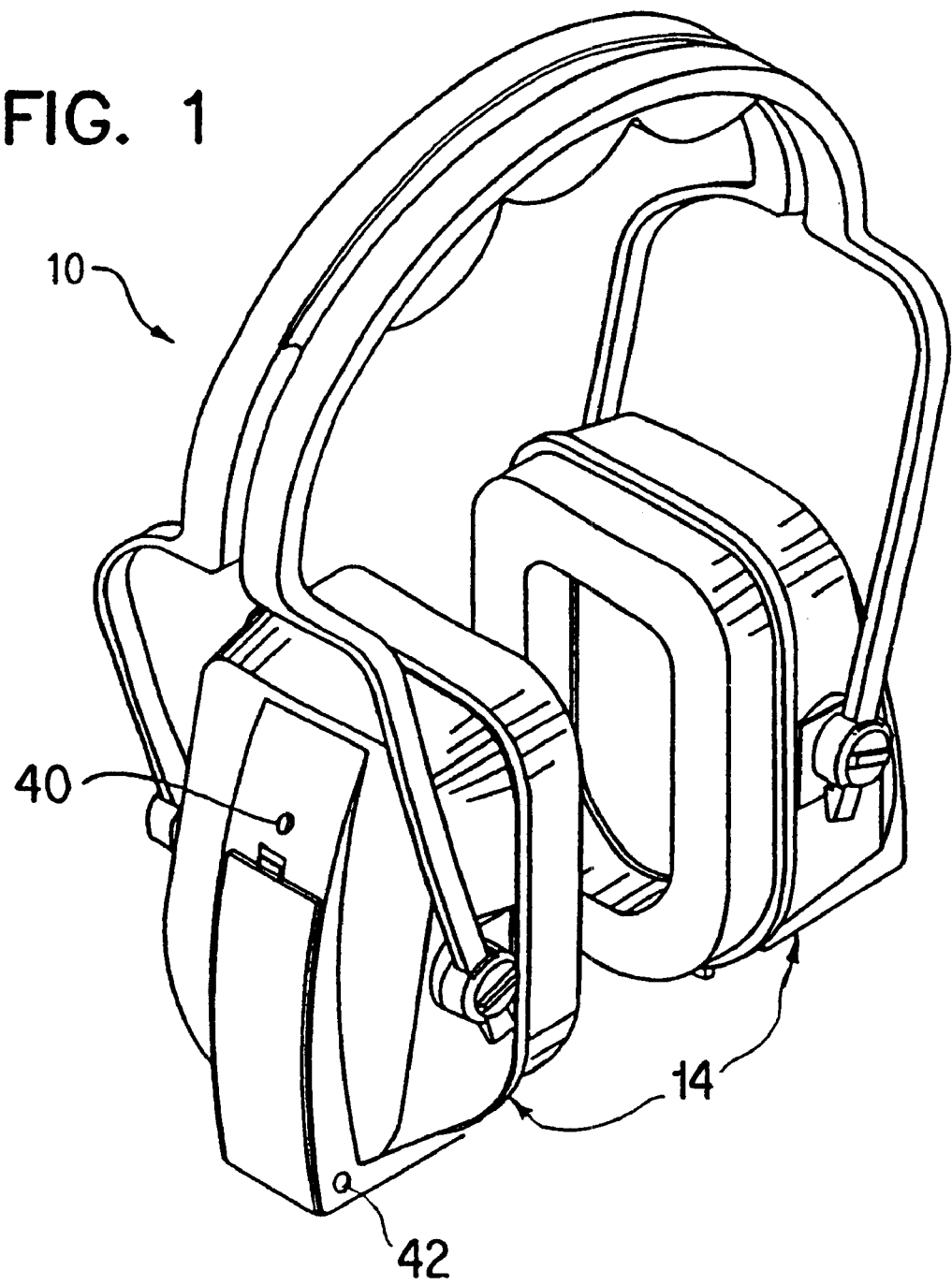
FIG. 1 is an isometric view of a muff-type embodiment of the continuous noise monitoring and reduction system of the present invention.
Figure 2:
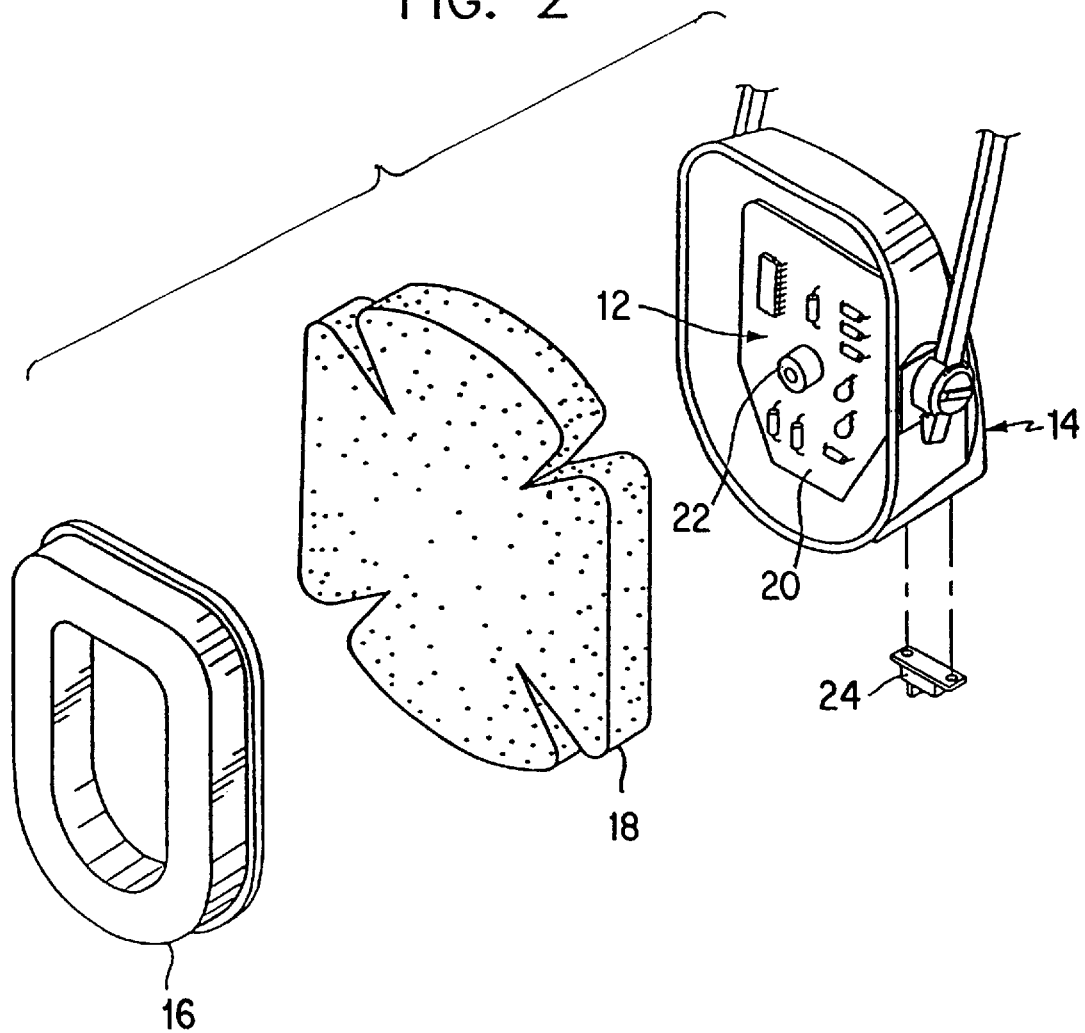
FIG. 2 is a partial, exploded view of the embodiment shown in FIG. 1.

Referring now to the drawings, FIG. 1 illustrates a muff-type embodiment of the continuous noise monitoring and reduction system of the present invention generally at 10. In this embodiment of the invention, the noise dosimetry hardware, illustrated generally at 12 in FIG. 2, is housed entirely within the cup 14 of the hearing protector. The electronics and microphone placement are designed to ensure that accurate exposure measurements are obtained when the CMD is worn in both a primary position or secondary position.

Figure 6:
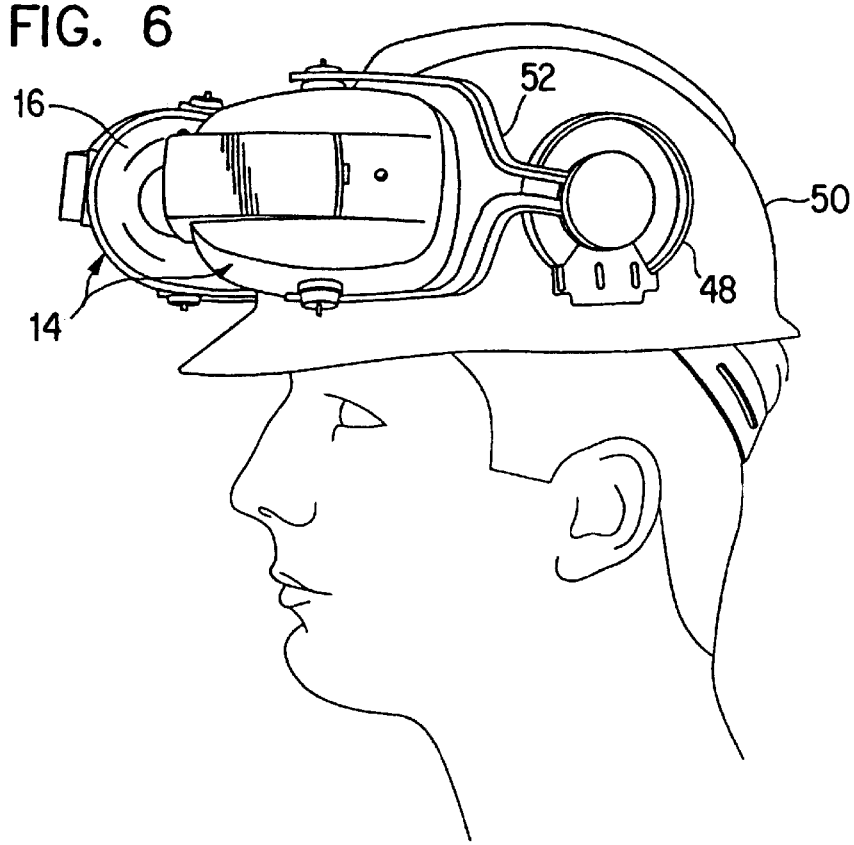
FIG. 6 illustrates an alternative embodiment of the invention depicting a safety cap mounted CMD in a secondary position wherein the muff-cups are positioned off the ear and in a forwardly extending position.

The muff-type configuration of the present invention may be embodied in many forms as illustrated by attachment of cups 14 to a flexible headband (see FIG. 1), or by attachment to a modified hardhat (see FIG. 6). Each cup 14 is preferably made of a high-impact, shock-resistant, and durable plastic, and is fitted with an oval-shaped cushion 16 with an opening for accommodating the wearer's ears. Cushion 16 is attached to cup 14 by snapping or gluing it into place, and is designed to reduce environmental noise reaching the wearer's ears. Open-cell foam 18 damps vibration and helps to reduce the noise level inside cup 14.

The interior cavity of cup 14 encloses a circuit board 20, mounted via a metal frame to the interior surface of the cup. A microphone 22, connected to circuit board 20, measures the noise impinging on the ear of the user when the CMD is being worn in a primary position over the ear, as well as in the secondary position wherein the device is worn off the ear. The noise dosimetry hardware 12, positioned on circuit board 20, is made functional by a switch 24 located on the exterior of cup 14. Switch 24 can be a rocker-type switch or a sliding switch.

Figure 3:
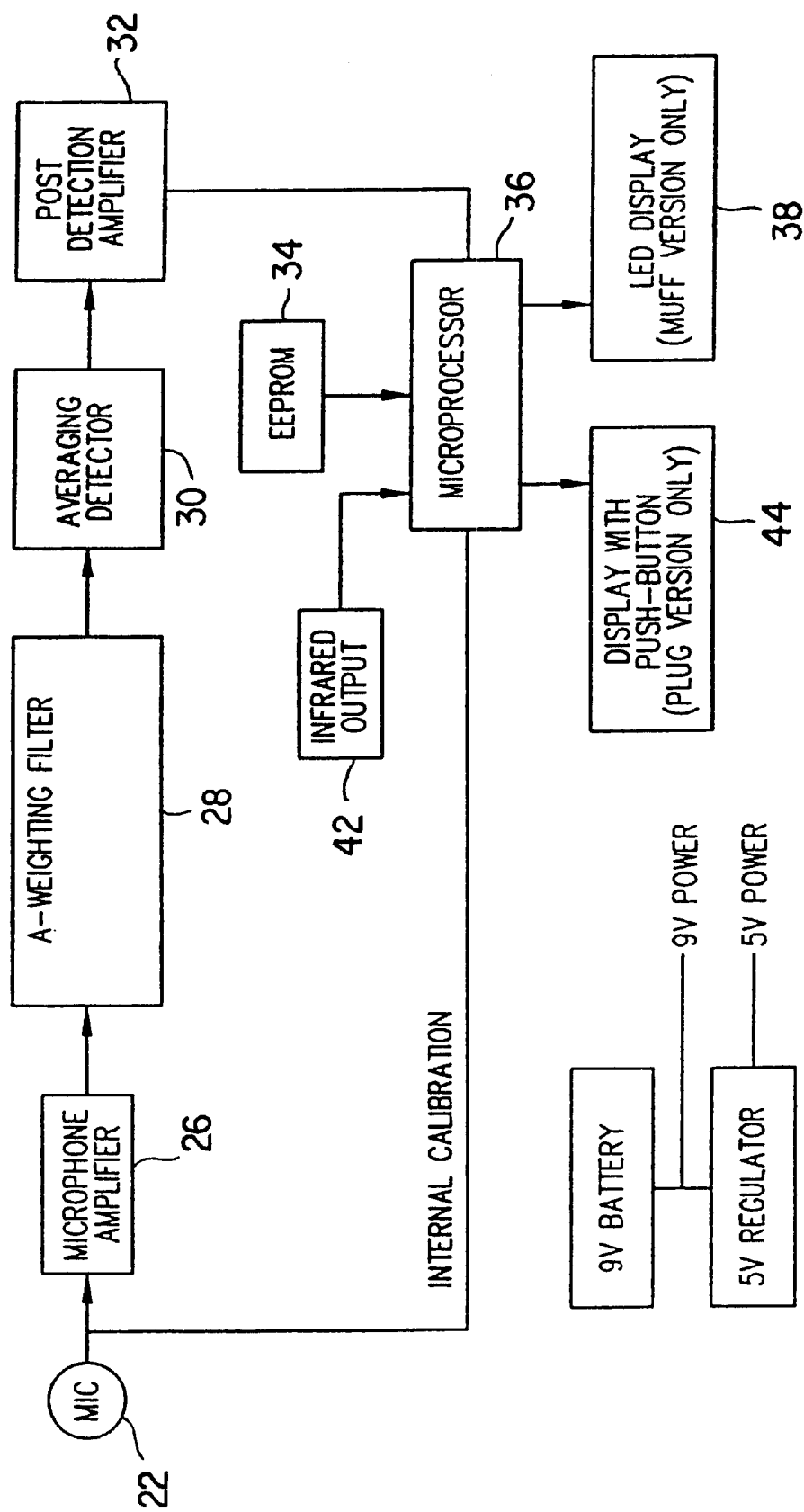
FIG. 3 is a block diagram/flow chart of the electronic components embodying the principles of the present invention.
Figure 4A:
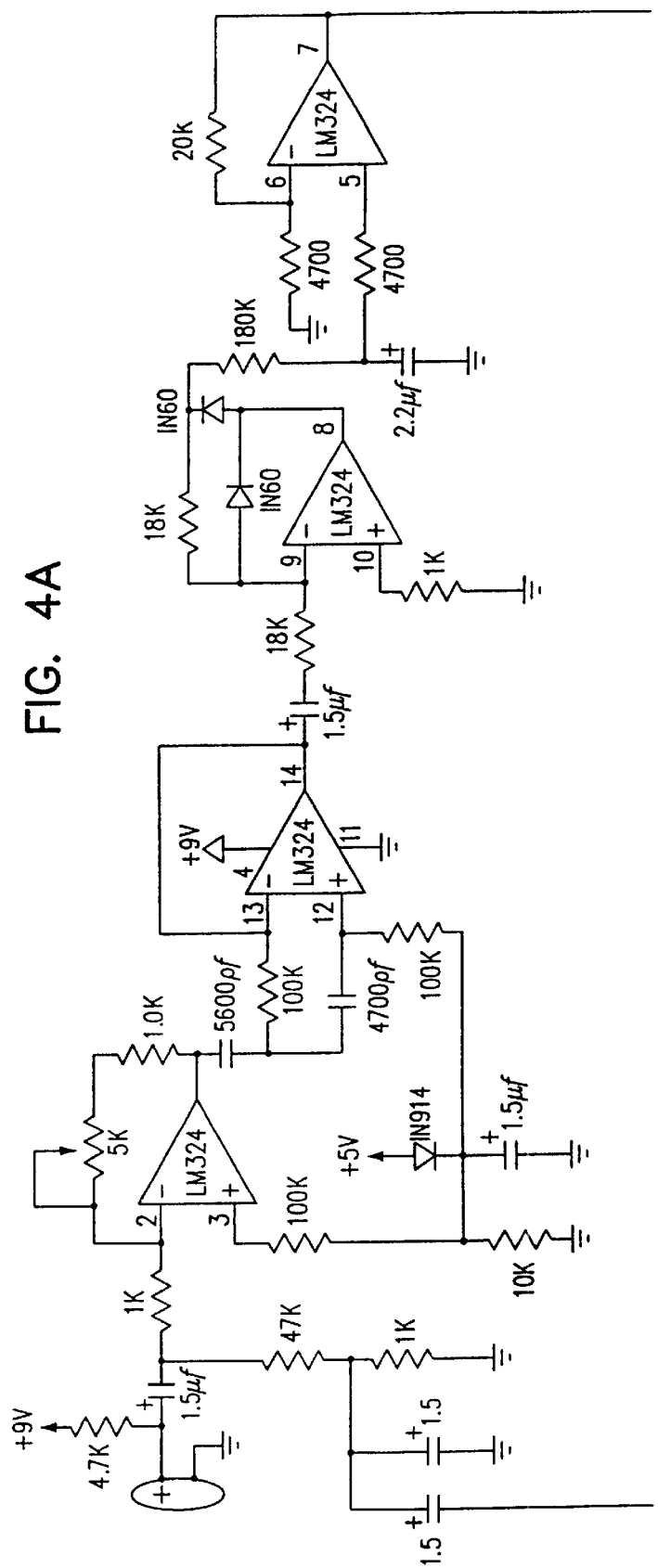
FIGS. 4A & 4B show an electronic circuit schematic diagram illustrating the electronics for a muff-type CMD.
Figure 4B:
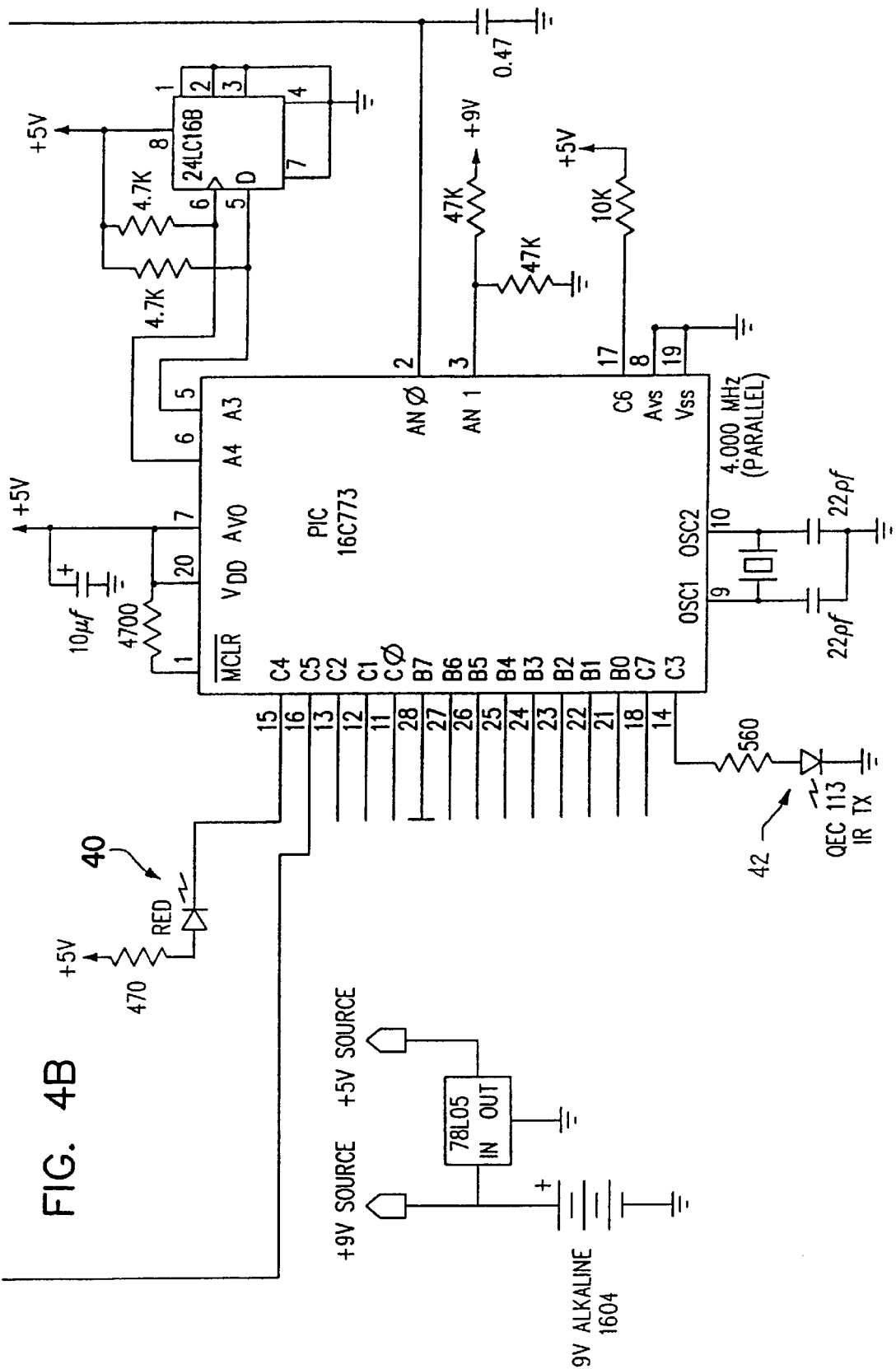
Figure 5:
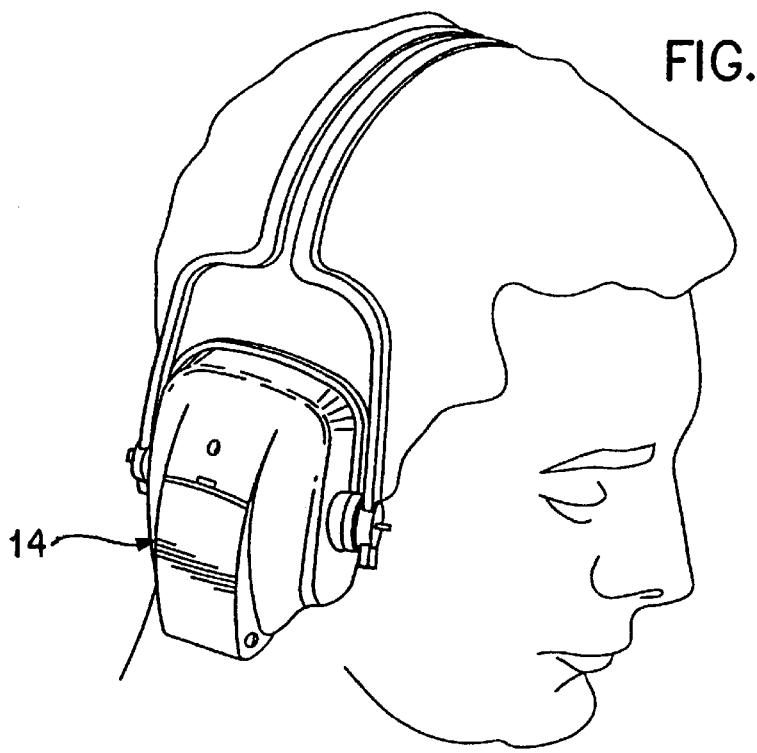
FIG. 5 is an illustration of the embodiment of the invention shown in FIG. 1 depicting a muff-type CMD in a primary position wherein the muff-cups are positioned in a downwardly extending position to occlude the ear.
Figure 10A:
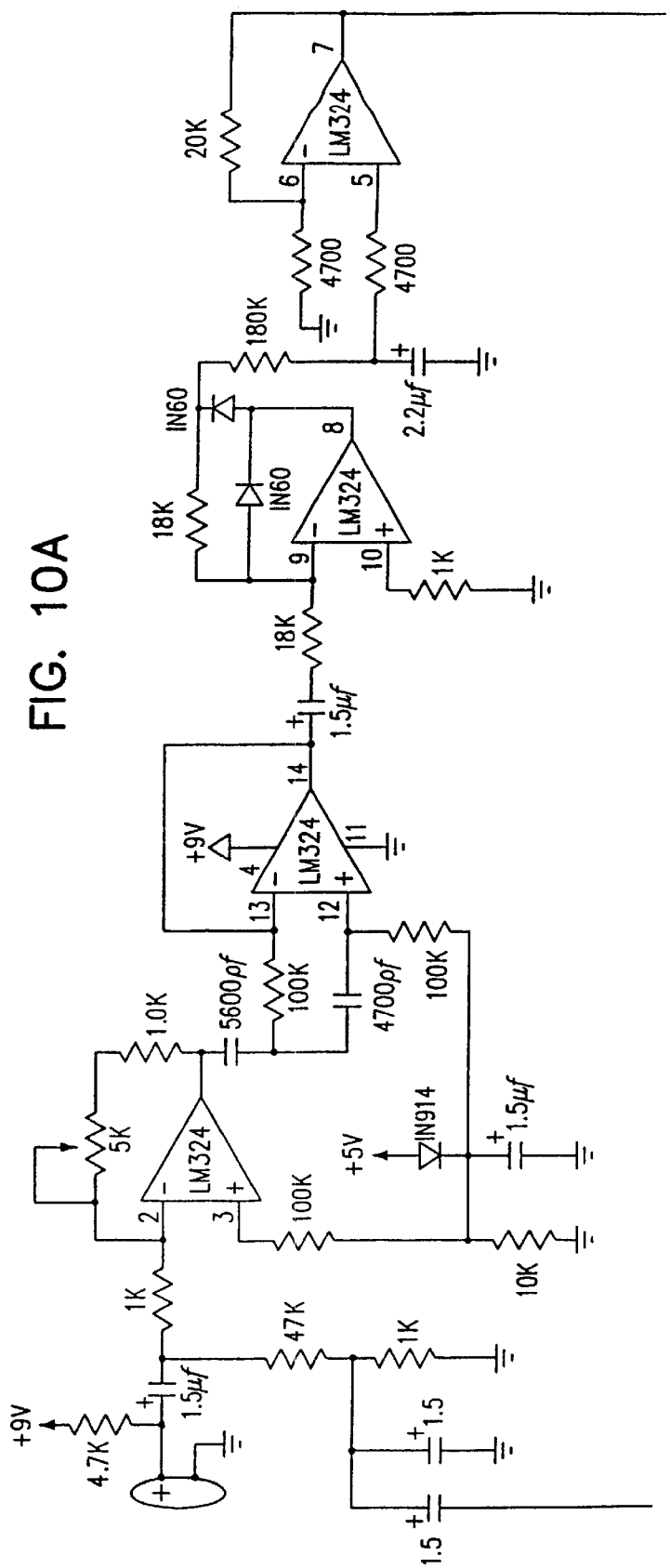
FIGS. 10A & 10B show an electronic circuit schematic diagram illustrating the electronics for an insert-type CMD.
Figure 10B:
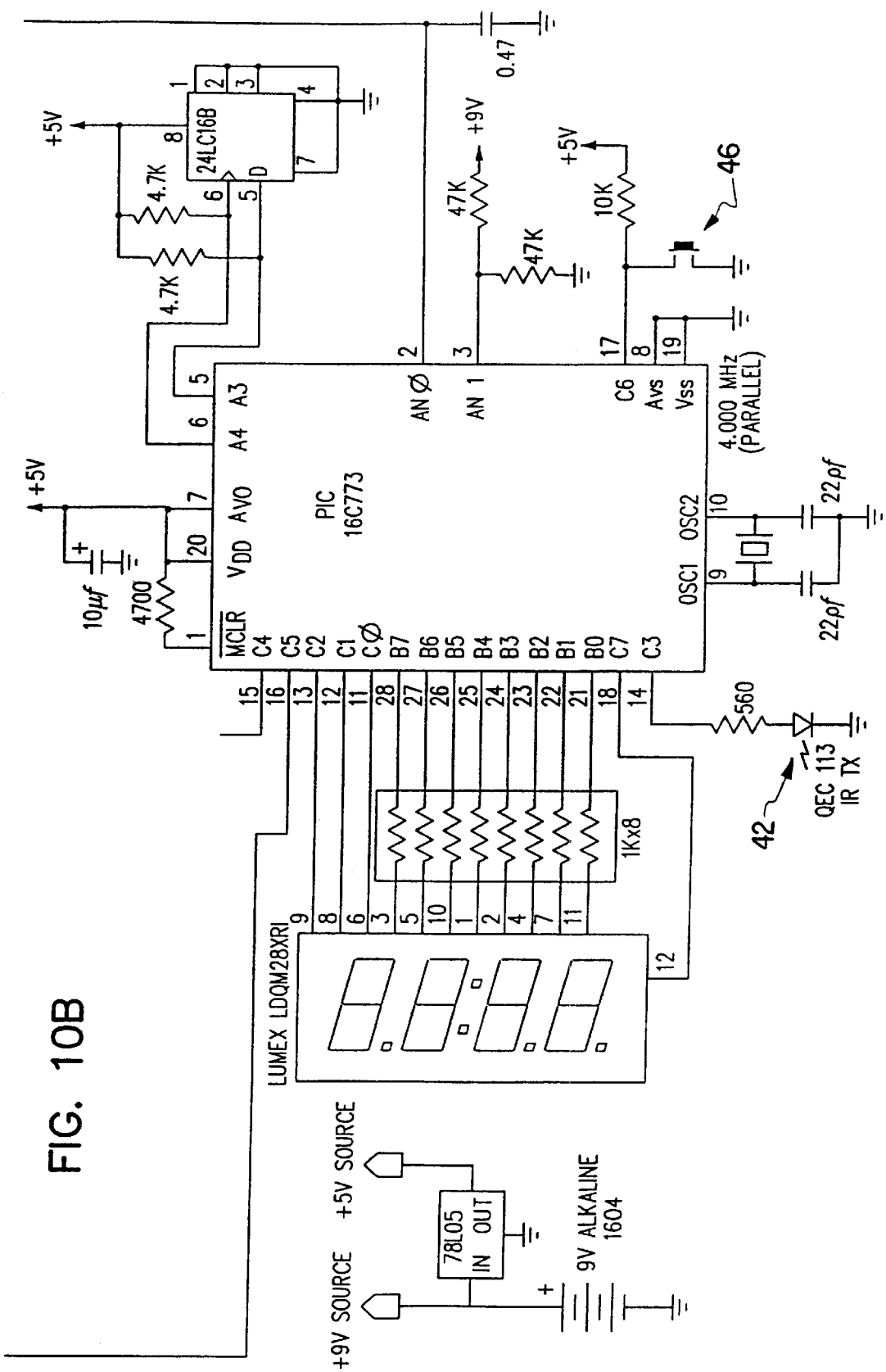

Referring now primarily to FIGS. 3, 4, and 10, the electronic components of the invention are relatively simple. A microphone 22 senses the sound pressure level incident upon it (and equivalent to that incident upon a user's ears), and converts the sound into an electrical signal which includes the duration, magnitude, and other variables of the sound pressure level. The electrical signal is then amplified by a microphone amplifier circuit 26, and modified by an A-weighting filter 28 so that the signal is more representative of the damage risk to the human auditory system. This modification is primarily done by de-emphasizing the low frequency components of the acoustic signal, and is required for comparison to Occupational Safety and Health Administration ("OSHA") limits. The "A" weighting represents a standard measure of the relative sound level (dB) for a given frequency.

The A-weighted signal is converted to a DC voltage by an averaging-type detector circuit 30, and amplified by a post-detection amplifier circuit 32. The resulting electrical signal corresponds to a specific sound pressure level reflecting that which is incident upon the ear of the individual user both when the HPD is being worn in, or over the ears, as well as when it is in the secondary, off-the-ear position.

The noise monitoring and reduction system of the present invention continuously monitors the sound level incident upon the user's ears via the microphone and electronics just described, and records the data in an EEPROM chip 34. Microprocessor 36 makes continuous evaluations of the user's total noise dose based on the incoming signals and the time of exposure, and compares the total noise does against a preset-action level, i.e., 85 dBA TWA (85 dBA TWA is generally considered the maximum "safe" noise dose for preventing noise induced hearing loss). Some industries may choose a higher preset level that would correspond to a permissible exposure level pursuant to government regulations, or beyond which, expenditures for engineering controls would have to be made.

When the total noise dose reaches the preset-action level, a warning indicator is triggered as discussed previously which may be aural, visual, or tactile. Tactile warnings may be preferable because audio alarms may contribute to hearing damage, whereas visual alarms may not be immediately recognized, or may be difficult to see depending on their location.

Figure 7:
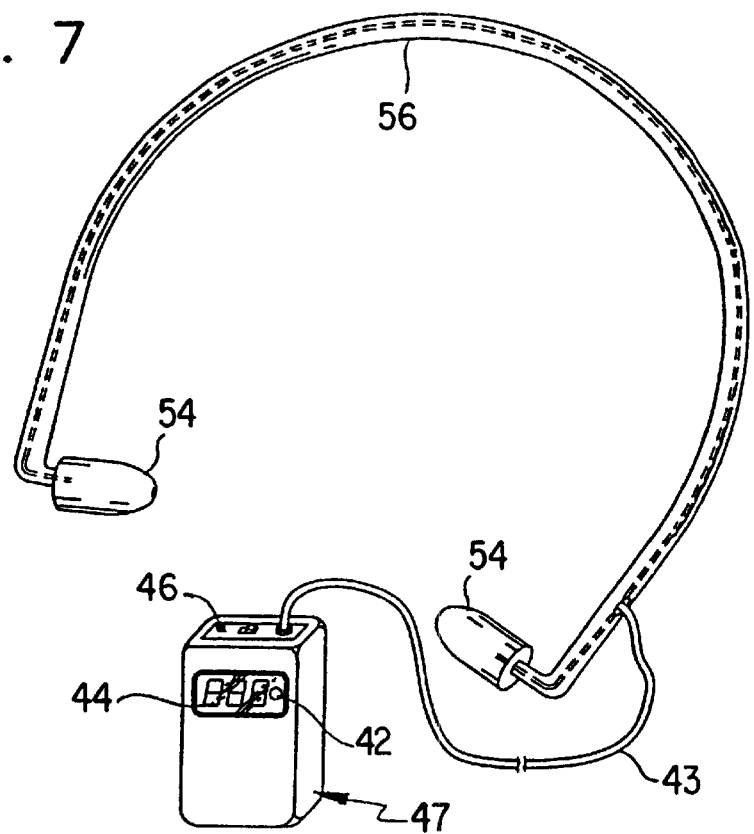
FIGS. 7 and 8 illustrate additional embodiments of the present invention in the form of semi-aural and insert-type CMDs.
Figure 8:
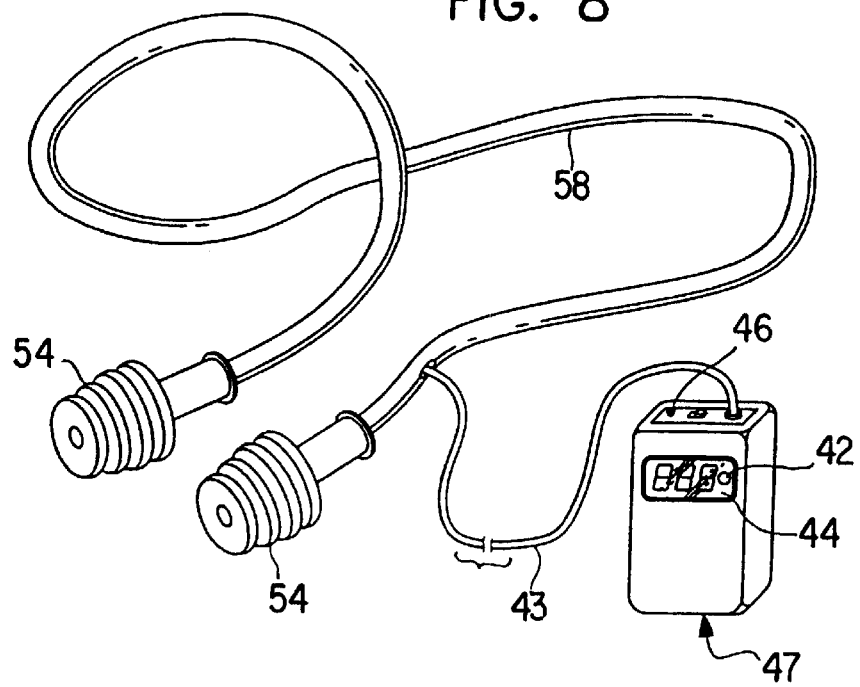

The basic difference between the muff-type electronics and the electronics of the insert-type embodiments illustrated in FIGS. 7 and 8 is the display of information. The muff-type embodiment is equipped only with an LED display 38 wherein one LED 40 (see FIG. 1) indicates when the wearer's noise dose is approaching the preset action level at which point administrative action should be taken. Another LED 42 functions as the infrared ("IR") output for data transfer to an IR receiver connected to a PC (not shown). It should be noted that it is also possible to mount only the microphone(s) in the cup(s) of muff-type devices, and to maintain the electronics externally, as is done with the insert-type CMD. In some instances, this may be preferred due to weight considerations.

The insert-type embodiment is equipped with a digital display 44 activated by user actuation of a push button 46 (see FIGS. 7, 8, and 10). The insert-type electronics and display, with the exception of the microphone, are located in a separate dosimeter 47 which may be located in the user's pocket. Actuation of the push button 46 will provide the user with a display of the current cumulative noise dose the user has received, the current A-weighted sound pressure level, or the number of hours that the unit has been collecting data. The insert-type embodiment's dosimeter 47 is also equipped with an IR output diode 42 for data transfer to an IR receiver which may be connected to a PC, as with the muff-type embodiment.

Referring now to FIG. 6 which illustrates an alternative muff-type embodiment wherein the dosimetry measurement hardware is housed within the cup 14 of a muff-type safety cap-mounted hearing protector. When the cups are removed from the user's ears to the secondary position, they are rotated upwards so that they extend straight up, forward or backward. A flanged ring 48, mounted to safety cap 50, prevents forked member 52 from converging toward the surface of cap 50, and maintains cup 14 in a position spaced apart from cap 50. This spacing arrangement ensures that oval cushion 16 cannot rest against cap 50 thereby preventing an inaccurate sound level measurement from the secondary position of the CMD. Again, the microphone circuitry and placement have been designed to ensure that accurate measurements are made while the safety cap-mounted CMD is in the primary position (occluding the ear) and when it is in the secondary (off the ear) position.

Turning our attention now to a pair of insert-type embodiments illustrated in FIGS. 7 and 8, the microphone 60 (see FIG. 9) of the noise dosimeter is placed near the distal end 74 (see FIG. 9) of an insert-type hearing protector (i.e., ear plug) with a tube 66 (see FIG. 9) and acoustic filter 67 (see FIG. 9) located between the microphone and the tip of the plug. Referring specifically to FIG. 7, the insert-type CMD may include mounting the ear plugs 54 to the end of a band connector 56, forming a semi-aural type hearing protector. In this particular embodiment, the user would keep the device around his or her neck when the plugs are not donned, thereby providing a convenient secondary wearing position. The microphone or microphones are connected to the separate dosimeter hardware 47 by electrical wires 43 or other suitable means for communicating the microphone's signal to the dosimeter circuit.

FIG. 8 illustrates an alternate embodiment of the insert-type CMD wherein a flanged silicon ear plug 54 is located at the end of a retaining string 58. The retaining string 58 serves to prevent the plugs 54 from falling off the user, and to maintain the CMD in a secondary wearing position when the plugs are removed from the ear. The secondary position for this insert-type embodiment may be defined by the plugs resting on the user's chest with the tip 68 of tube 66 (see FIG. 9) exposed to the ambient noise. These noise level measurements equate to the sound pressure levels incident on the user's ear. The string 58 also consists of or contains the conducting wires 43 for connecting the microphone(s) located inside the plugs 54 to the separate dosimeter hardware 47. The separate dosimeter electronics are located remotely either on the user, or mounted to the band connector 56 of the semi-aural CMD, or retaining string 58 of the insert-type CMD.

Referring now to FIG. 9, a cross-sectional view of a typical insert-type CMD is illustrated showing the location of the microphone and its enclosure within the ear plug. Microphone 60 is housed within a two-piece tubular enclosure consisting of an inner enclosure 71 and an outer enclosure 62. Outer enclosure 62 is connected to a narrow tube 66 that extends to a tip 68 at the end of ear plug 54. The tip 68 of tube 66 is flush with the proximal (inserted) end 70 of a typical ear plug 54 and creates a channel through which the sound pressure level impinging upon the user's ear can be measured by the microphone. An acoustic filter 67 is positioned within the tube 66 to damp acoustic resonance within the tube. The acoustic filter 67 is essentially an acoustic resistor generally consisting of a hollow metal cylinder filled with a fiber material that predictably reduces sound pressure level by specific amounts across specific frequency ranges. The resistive value of the filter 67 required to damp acoustic resonance within the tube 66 varies with the length of the tube, and the length of the tube varies with the type of plug selected by a user. A typical plug to be used as part of an insert-type or semi-aural CMD will require a filter with a resistance in the range of 680–1500 Ohms. Acoustic filters of this type are commercially available from Knowles Electronics of Itasca, Ill.

The outer microphone enclosure 62 preferably extends longitudinally at the proximal end 64 to create a cylinder 65 capable of receiving the end 69 of the tube 66 as illustrated in FIG. 9. The acoustic filter 67 is separately placed into the tube 66 near the center of the plug 54. The outer enclosure 62 may alternatively be extended to form a cylinder which totally or partially replaces the tube 66 with an integral microphone enclosure and tube. Extending the outer enclosure 62, as described, to form an integral microphone enclosure and tube has the advantage of providing a pre-assembled housing for the acoustic filter 67. In the case where the integrated unit does not totally replace the tube 66, a shorter tube is still employed in a manner such as was previously described. In either case, the resistance of the filter 67 varies with the tube length, whether it be comprised of one or more pieces, in order to properly damp acoustic resonance within the tube. In a preferred embodiment, a 3-flange silicon reusable insert-type plug is fitted with a tube 1.9 cm. in length. An acoustic filter with a resistance of 1500 Ohms is then placed inside the tube 66 0.9 cm. from the microphone 60. This length corresponds to the distance between the face of the microphone and the center of the filter. The filter 67 may be placed within the range of 0.7 cm. to 1.1 cm. from the microphone in order to damp acoustic vibrations within the tube, but a placement of 0.9 cm. has proven to be most effective.

The electrical connection 72 for the microphone 60 extends through the distal end 74 of the ear plug 54 to transmit signals to the external dosimeter (see FIGS. 7 and 8). The electrical connection 72 is supported at the point of connection with the microphone 60 by inner tubular enclosure 71 which surrounds the microphone 60 to a point preferably flush with the face of the microphone. Enclosure 71 serves three primary functions: 1) it adapts the diameter of the microphone so that it fits standard dosimeter calibrators; 2) it houses and provides strain relief for the connection point of the electrical wires that connect the microphone to the dosimeter circuit; and 3) it provides a mechanism for the microphone to be solidly attached to the headband when used in a semi-aural configuration as illustrated in FIG. 9A. FIG. 9A shows the lower portion of a headband similar to that illustrated in FIG. 7, indicated by reference numeral 57, connected to a portion of inner enclosure 71 which surrounds and supports electrical connection 72. As illustrated by FIGS. 7 and 9A, the electrical connection indicated at 43 and 72 respectively, may or may not be partially enclosed by the headband 56 (see FIG. 7). The microphone 60, tubular enclosures 62, 71, tube 66, and acoustic filter 67 may be inserted into the ear plugs following molding so that the microphone hardware can be easily removed and inserted into a new set of ear plugs when the old plugs are worn or discarded.

In any embodiment of the invention, it is possible to monitor the exposure of both ears, or only one ear. This two microphone system would allow for binaural measurements in either the insert-type or muff-type embodiments. In the muff-type embodiment, CMD measurement hardware can be mounted in each earcup. In the insert-type embodiment, an additional dosimeter hardware package can be carried by the user. Alternatively, since the CMD is multi-channel microprocessor based, it is possible for the hardware to sample two microphones with minimal additional circuitry, thereby alleviating the need for duplicative dosimeter electronics.

In still another embodiment of the invention, two microphones could be used for each ear's measurements. One microphone would be used to measure noise exposure near the entrance to the ear, and the other to measure noise exposure when the HPD is removed from the ear. By way of example, one microphone could be positioned inside the cup 14 of a muff-type CMD (see FIG. 1) while the other is located on the external shell of the cup. A switch would then direct the signal from the appropriate microphone to the dosimeter electronics for recordation and evaluation of the accumulated noise dose. The signal from the internal microphone would be sampled while the CMD is worn in the primary position, while the external microphone would be sampled when the CMD is removed and worn in the secondary position.

It will be apparent to the reader that the invention may be embodied in many forms in addition to those disclosed herein without departing from the spirit or essential characteristics of the invention. The present embodiment is therefore to be considered in all respects as illustrative and not restrictive. The scope of the invention is indicated by the appended claims rather than by the foregoing description and the drawings, and all changes which come within the meaning and range of equivalency of the claims are therefore intended to be embraced therein.

What is claimed is:

1. A hearing protector and continuous noise monitoring system, to be worn at either a primary position or a secondary position, the system comprising:
    at least one microphone positioned such that the microphone detects a protected noise exposure in the primary position and an unprotected noise exposure in the secondary position.

2. A hearing projector and continuous noise monitoring system as defined in claim 1, selected from the group consisting of ear-muffs, ear-plugs, and semi-aural devices.

3. A system according to claim 1, further comprising an electronic conversion circuit electrically connected to the microphone, the conversion circuit being operative to convert the noise into a signal representative of the risk to the human auditory system.

4. A hearing protector and continuous noise monitoring system as defined in claim 3, wherein the electronic conversion circuit comprises a microphone amplifier circuit electrically connected to an A-weighting filter circuit, the A-weighting filter circuit being electrically connected to an averaging-type detector circuit, the averaging-type detector circuit being electrically connected to a post detection amplifier circuit.

5. A system according to claim 3, further comprising a data processing/storage module electrically connected to the electronic conversion circuit, wherein the module calculates and records a cumulative dose from the signal.

6. A system according to claim 5, further comprising a warning indicator electrically connected to the data processing/storage module, wherein the processing/storage module compares the cumulative noise dose against a preset level, and the warning indicator is activated when the cumulative noise dose exceeds the preset level.

7. A hearing protector and continuous noise monitoring system as defined in claim 6, wherein the warning indicator is a visual indicator.

8. A hearing protector and continuous noise monitoring system as defined in claim 6, wherein the warning indicator is an audible indicator.

9. A hearing protector and continuous noise monitoring system as defined in claim 6, wherein the warning indicator is a tactile indicator.

10. A system according to claim 5, further comprising a transmitter operative to transmit the measure of cumulative noise dose from the data processing/storage module to a data storage and retrieval device.

11. A hearing protector and continuous noise monitoring system as defined in claim 10, wherein the transmitter comprises an infrared output LED.

12. A hearing protector and continuous noise monitoring system as defined in claim 10, wherein the data storage and retrieval device is a computer with an interconnected infrared receiver.

13. A hearing protector and continuous noise monitoring system as defined in claim 5, wherein the cumulative noise dose is expressed as a percentage daily dose, or a time-weighted average dose.

14. A system according to claim 1, wherein the system comprises two microphones allowing binaural detection of the protected and unprotected exposures.

15. A hearing protector and continuous noise monitoring system comprising:
a first microphone positioned to detect a protected noise exposure, and a second microphone positioned to detect an unprotected noise exposure; and
a switch that selectively connects the first and second microphones to an electronic conversion circuit, the switch being positionable to connect the first microphone to the conversion circuit when the hearing protector is worn in a primary position, and the switch being positionable to connect the second microphone to the conversion circuit when the hearing protector is being worn in a secondary position;
the electronic conversion circuit capable of converting the noise into a signal representative of the risk to the human auditory system.

16. A hearing protector and continuous noise monitoring system as defined in claim 15, selected from the group consisting of ear-muffs, ear-plugs, and semi-aural devices.

17. A hearing protector and continuous noise monitoring system as defined in claim 15 wherein the electronic conversion circuit comprises a microphone amplifier circuit electrically connected to an A-weighting filter circuit, the A-weighting filter circuit being electrically connected to an averaging-type detector circuit, the averaging-type detector circuit being electrically connected to a post detection amplifier circuit.

18. A system according to claim 15, further comprising a data processing/storage module electronically connected to the electronic conversion circuit, wherein the module records and calculates a cumulative noise dose from the signal, and compares the measure of cumulative noise dose against a preset level.

19. A system according to claim 18, further comprising a warning indicator electrically connected to the data processing/storage module activated when the measure of cumulative noise dose exceeds the preset level.

20. A system according to claim 19, further comprising a transmitter for transmitting the measure of cumulative noise dose from the data processing/storage module to a data storage and retrieval device.

21. A hearing protector and continuous noise monitoring system as defined in claim 20, wherein the transmitter comprises an infrared output LED.

22. A hearing protector and continuous noise monitoring system as defined in claim 20, wherein the data storage and retrieval device is a computer with an interconnected infrared receiver.

23. A hearing protector and continuous noise monitoring system as defined in claim 19, wherein the warning indicator is a visual indicator.

24. A hearing protector and continuous noise monitoring system as defined in claim 19, wherein the warning indicator is an audible indicator.

25. A hearing protector and continuous noise monitoring system as defined in claim 19, wherein the warning indicator is a tactile indicator.

26. A hearing protector and continuous noise monitoring system as defined in claim 18, wherein the cumulative noise dose is expressed as a percentage daily dose, or as a time-weighted average dose.

27. A system according to claim 15, the system further comprising a third microphone, wherein the first and the third microphones allow binaural detection of the protected exposures.

28. A method for monitoring an individual's noise exposure comprising the steps of:
measuring a protected noise exposure level and an unprotected noise exposure level incident upon the ear of the individual;
calculating the individual's cumulative noise exposure dose for a given period of time;
comparing the cumulative noise exposure dose to a preset dose level; and
alerting the individual when the cumulative exposure noise dose exceeds the preset level.

29. A method as defined in claim 28 further comprising the step of transmitting the cumulative noise dose to a data storage and retrieval device.

30. The method of claim 28, wherein the noise exposure level is converted to an electronic signal, the signal being adjusted to an A-weighted sound level.

* * * * *